(12) United States Patent
Barere et al.

(10) Patent No.: US 10,940,273 B2
(45) Date of Patent: Mar. 9, 2021

(54) INJECTION SENSOR WITH FEEDBACK MECHANISM

(71) Applicant: LifeCell Corporation, Madison, NJ (US)

(72) Inventors: Aaron M. Barere, Hoboken, NJ (US); Evan J. Friedman, West Orange, NJ (US)

(73) Assignee: LifeCell Corporation, Madison, NJ (US)

( * ) Notice: Subject to any disclaimer, the term of this patent is extended or adjusted under 35 U.S.C. 154(b) by 132 days.

(21) Appl. No.: 16/140,861

(22) Filed: Sep. 25, 2018

(65) Prior Publication Data

US 2019/0022335 A1 Jan. 24, 2019

Related U.S. Application Data

(63) Continuation of application No. 14/682,342, filed on Apr. 9, 2015, now Pat. No. 10,092,711.

(60) Provisional application No. 61/987,914, filed on May 2, 2014.

(51) Int. Cl.
*A61M 5/48* (2006.01)
*A61M 5/145* (2006.01)
*A61M 5/315* (2006.01)
*A61M 5/31* (2006.01)

(52) U.S. Cl.
CPC .......... *A61M 5/486* (2013.01); *A61M 5/1458* (2013.01); *A61M 5/31511* (2013.01); *A61M 5/48* (2013.01); *A61M 2005/3125* (2013.01); *A61M 2202/08* (2013.01); *A61M 2205/18* (2013.01); *A61M 2205/3331* (2013.01); *A61M 2205/50* (2013.01); *A61M 2205/582* (2013.01)

(58) Field of Classification Search
CPC .... A61M 5/48; A61M 5/486; A61M 2205/18; A61M 2205/50; A61M 2205/3331
See application file for complete search history.

(56) References Cited

U.S. PATENT DOCUMENTS

| | | |
|---|---|---|
| 3,791,524 A | 2/1974 | Cho |
| 4,064,879 A | 12/1977 | Leibinsohn |
| 4,346,708 A | 8/1982 | LeVeen et al. |
| 4,624,659 A | 11/1986 | Goldberg et al. |
| 4,681,571 A | 7/1987 | Nehring |
| 4,753,634 A | 6/1988 | Johnson |

(Continued)

FOREIGN PATENT DOCUMENTS

| | | |
|---|---|---|
| EP | 0512769 A2 | 11/1992 |
| EP | 1825876 A1 | 8/2007 |

(Continued)

OTHER PUBLICATIONS

Coleman et al., Fat grafting to the breast revisited: safety and efficacy. Plast Reconstr Surg. Mar. 2007;119(3):775-85.

(Continued)

*Primary Examiner* — Laura A Bouchelle
*Assistant Examiner* — Anh Bui
(74) *Attorney, Agent, or Firm* — McCarter & English, LLP

(57) ABSTRACT

The present disclosure provides devices for implanting tissue or other substances within the body. The devices can include a feedback mechanism, which can assist a surgeon in implanting the tissue or other substances by preventing excess shear force or pressure on the tissue or substance to be implanted.

19 Claims, 3 Drawing Sheets

(56) References Cited

U.S. PATENT DOCUMENTS

| | | |
|---|---|---|
| 4,759,750 A | 7/1988 | DeVries et al. |
| 5,301,685 A | 4/1994 | Guirguis |
| 5,330,914 A | 7/1994 | Uhlen et al. |
| 5,336,616 A | 8/1994 | Livesey et al. |
| 5,372,945 A | 12/1994 | Alchas et al. |
| 5,409,833 A | 4/1995 | Hu et al. |
| 5,610,074 A | 3/1997 | Beritashvili et al. |
| 5,785,640 A | 7/1998 | Kresch et al. |
| 5,786,207 A | 7/1998 | Katz et al. |
| D401,336 S | 11/1998 | Muller et al. |
| 5,901,717 A | 5/1999 | Dunn et al. |
| 5,968,356 A | 10/1999 | Morsiani et al. |
| D424,194 S | 5/2000 | Holdaway et al. |
| 6,200,606 B1 | 3/2001 | Peterson et al. |
| 6,258,054 B1 | 7/2001 | Mozsary et al. |
| 6,261,549 B1 | 7/2001 | Fernandez et al. |
| 6,478,966 B2 | 11/2002 | Zhou et al. |
| 6,544,788 B2 | 4/2003 | Singh |
| 6,733,537 B1 | 5/2004 | Fields et al. |
| D492,995 S | 7/2004 | Rue et al. |
| 6,852,533 B1 | 2/2005 | Rafii et al. |
| 7,172,572 B2 | 2/2007 | Diamond et al. |
| 7,361,368 B2 | 4/2008 | Claude et al. |
| 7,390,484 B2 | 6/2008 | Fraser et al. |
| D575,393 S | 8/2008 | Stephens |
| 7,429,488 B2 | 9/2008 | Fraser et al. |
| 7,473,420 B2 | 1/2009 | Fraser et al. |
| 7,501,115 B2 | 3/2009 | Fraser et al. |
| 7,514,075 B2 | 4/2009 | Hedrick et al. |
| 7,585,670 B2 | 9/2009 | Hedrick et al. |
| 7,588,732 B2 | 9/2009 | Buss |
| 7,595,043 B2 | 9/2009 | Hedrick et al. |
| 7,651,684 B2 | 1/2010 | Hedrick et al. |
| 7,687,059 B2 | 3/2010 | Fraser et al. |
| 7,708,152 B2 | 5/2010 | Dorian et al. |
| 7,732,190 B2 | 6/2010 | Michal et al. |
| 7,744,820 B2 | 6/2010 | Togawa et al. |
| 7,749,741 B2 | 7/2010 | Bullen et al. |
| 7,780,649 B2 | 8/2010 | Shippert |
| 7,780,860 B2 | 8/2010 | Higgins et al. |
| 7,789,872 B2 | 9/2010 | Shippert |
| 7,794,449 B2 | 9/2010 | Shippert |
| 7,887,795 B2 | 2/2011 | Fraser et al. |
| 7,901,672 B2 | 3/2011 | Fraser et al. |
| 8,062,286 B2 | 11/2011 | Shippert |
| 8,100,874 B1 | 1/2012 | Jordan et al. |
| 8,291,768 B2 | 10/2012 | Spiegel et al. |
| 8,293,532 B2 | 10/2012 | Moynahan |
| 8,333,740 B2 | 12/2012 | Shippert |
| 8,366,694 B1 | 2/2013 | Jordan |
| D679,011 S | 3/2013 | Kitayama et al. |
| 8,409,860 B2 | 4/2013 | Moynahan |
| D683,851 S | 6/2013 | Greenhalgh |
| D687,549 S | 8/2013 | Johnson et al. |
| D692,559 S | 10/2013 | Scheibel et al. |
| 8,622,997 B2 | 1/2014 | Shippert |
| 8,632,498 B2 | 1/2014 | Rimsa et al. |
| 8,887,770 B1 | 11/2014 | Shippert |
| 9,314,568 B2 | 4/2016 | Gurtner et al. |
| 9,446,189 B2 | 9/2016 | Rimsa et al. |
| 2001/0030152 A1 | 10/2001 | Wright et al. |
| 2002/0188280 A1 | 12/2002 | Nguyen et al. |
| 2004/0005246 A1 | 1/2004 | Efthimiadis et al. |
| 2004/0097867 A1 | 5/2004 | Fraser et al. |
| 2005/0084961 A1 | 4/2005 | Hedrick et al. |
| 2006/0051865 A1 | 3/2006 | Higgins et al. |
| 2006/0150742 A1 | 7/2006 | Esnouf |
| 2006/0184119 A1 | 8/2006 | Remde et al. |
| 2006/0224144 A1 | 10/2006 | Lee |
| 2007/0106208 A1 | 5/2007 | Uber et al. |
| 2007/0225665 A1 | 9/2007 | Perez-Cruet et al. |
| 2007/0248575 A1 | 10/2007 | Connor et al. |
| 2008/0014181 A1 | 1/2008 | Ariff et al. |
| 2008/0050275 A1 | 2/2008 | Bischof et al. |
| 2008/0167613 A1 | 7/2008 | Khouri et al. |
| 2008/0281278 A1 | 11/2008 | Williams, Jr. et al. |
| 2009/0042267 A1 | 2/2009 | Park |
| 2009/0181104 A1 | 7/2009 | Rigotti et al. |
| 2009/0287190 A1 | 11/2009 | Shippert |
| 2009/0299328 A1 | 12/2009 | Mudd et al. |
| 2010/0174162 A1 | 7/2010 | Gough et al. |
| 2010/0179488 A1 | 7/2010 | Spiegel et al. |
| 2010/0268189 A1 | 10/2010 | Byrnes et al. |
| 2010/0285521 A1 | 11/2010 | Vossman et al. |
| 2010/0285588 A1 | 11/2010 | Stubbers et al. |
| 2011/0009822 A1 | 1/2011 | Nielsen |
| 2011/0117650 A1 | 5/2011 | Riordan |
| 2011/0172659 A1* | 7/2011 | Brannan ............ A61B 18/1477 606/42 |
| 2011/0198353 A1 | 8/2011 | Tsao |
| 2012/0003733 A1 | 1/2012 | Gueneron |
| 2012/0071828 A1 | 3/2012 | Tojo et al. |
| 2012/0209248 A1 | 8/2012 | Gurtner et al. |
| 2012/0214659 A1 | 8/2012 | Do et al. |
| 2012/0265171 A1 | 10/2012 | Thorne, Jr. et al. |
| 2013/0131635 A1 | 5/2013 | Rimsa et al. |
| 2013/0150825 A1 | 6/2013 | Rimsa et al. |
| 2013/0158515 A1 | 6/2013 | Austen, Jr. |
| 2013/0324966 A1 | 12/2013 | Park et al. |
| 2014/0350517 A1* | 11/2014 | Dominguez ...... A61M 5/31501 604/506 |
| 2015/0314081 A1 | 11/2015 | Barere et al. |
| 2017/0112981 A1 | 4/2017 | Friedman et al. |

FOREIGN PATENT DOCUMENTS

| | | |
|---|---|---|
| JP | 2009-189282 A | 8/2009 |
| JP | 2011-12581 A | 1/2011 |
| WO | 2009/055610 A1 | 4/2009 |
| WO | 2011/005679 A1 | 1/2011 |
| WO | 2011/052946 A2 | 5/2011 |
| WO | 2012/006587 A2 | 1/2012 |
| WO | 2012/019103 A2 | 2/2012 |
| WO | 2012/083412 A1 | 6/2012 |
| WO | 2012/109603 A1 | 8/2012 |
| WO | 2012/139593 A2 | 10/2012 |
| WO | 2012/155056 A1 | 11/2012 |
| WO | 2013/054165 A1 | 4/2013 |
| WO | 2013/090579 A1 | 6/2013 |
| WO | 2013/106655 A1 | 7/2013 |
| WO | 2014/033209 A1 | 3/2014 |
| WO | 2014/070525 A1 | 5/2014 |
| WO | 2014/190223 A2 | 11/2014 |

OTHER PUBLICATIONS

Delay et al., Fat injection to the breast: technique, results, and indications based on 880 procedures over 10 years. Aesthet Surg J. Sep.-Oct. 2009;29(5):360-76.

Lee et al., The Effect of Pressure and Shear on Autologous Fat Grafting. Plast Reconstr Surg. (May 2013);131:1125-1136.

Pakhomov et al., Hydraulically coupled microejection technique for precise local solution delivery in tissues. J Neurosci Methods. Sep. 15, 2006;155(2):231-40.

Smith et al., Autologous human fat grafting: effect of harvesting and preparation techniques on adipocyte graft survival. Plast Reconstr Surg. May 2006;117(6):1836-44.

Ting et al., A new technique to assist epidural needle placement: fiberoptic-guided insertion using two wavelengths. Anesthesiology. May 2010;112(5):1128-35.

Yoshimura et al., Cell-assisted lipotransfer for cosmetic breast augmentation: supportive use of adipose-derived stem/stromal cells. Aesthetic Plast Surg. Jan. 2008;32(1):48-55.

International Search Report and Written Opinion for Application No. PCT/US2015/025035, dated Jun. 16, 2015.

International Preliminary Report on Patentability for Application No. PCT/US2013/041111, dated Dec. 11, 2014.

(56) References Cited

OTHER PUBLICATIONS

International Search Report and Written Opinion for Application No. PCT/US2014/039265, dated Nov. 18, 2014. 18 pages.

* cited by examiner

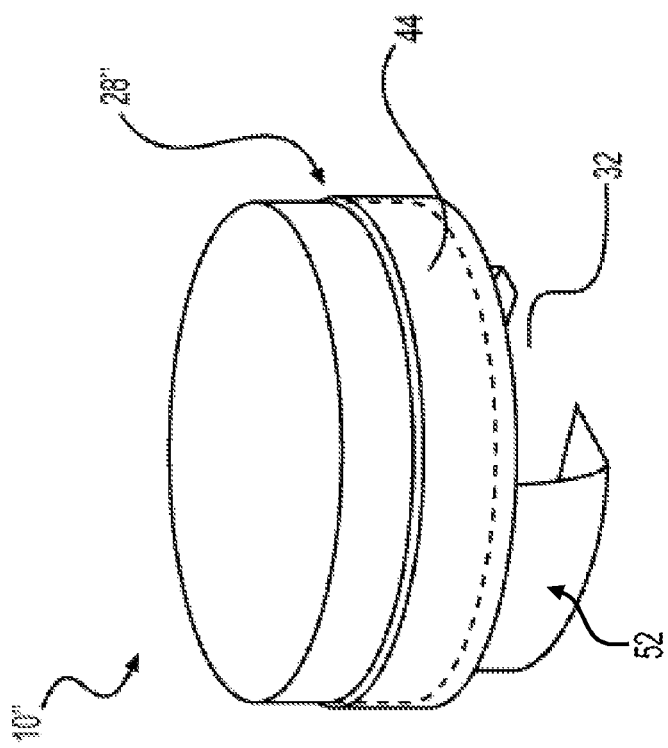
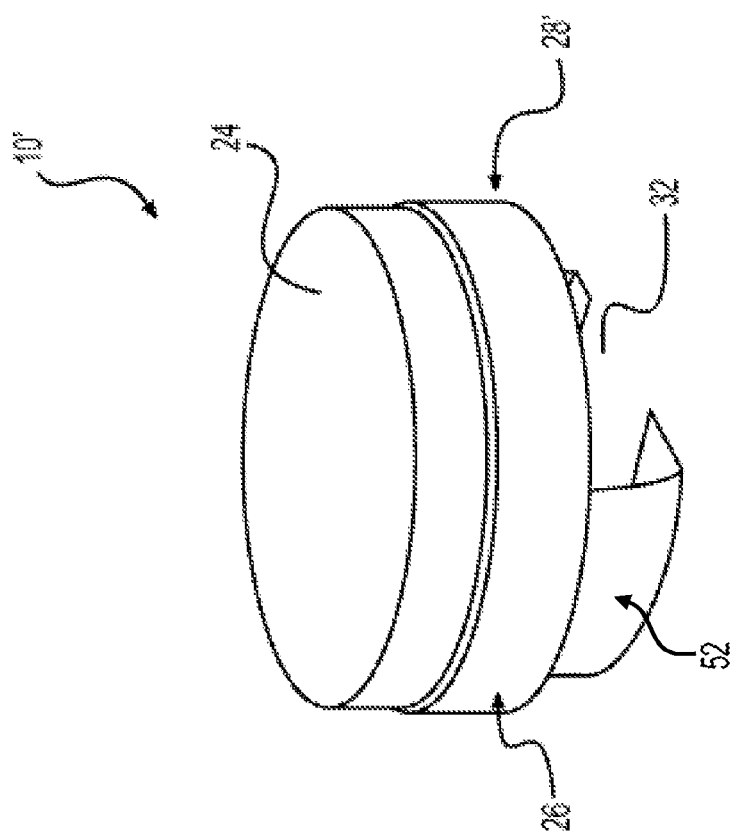

INJECTION SENSOR WITH FEEDBACK MECHANISM

CROSS-REFERENCE TO RELATED APPLICATIONS

This application is a continuation of U.S. patent application Ser. No. 14/682,342 (now U.S. Pat. No. 10,092,711), filed Apr. 9, 2015, which itself claims benefit under 35 U.S.C. § 119(e) of U.S. Provisional Application No. 61/987,914, filed May 2, 2014, each of which is herein incorporated by reference in its entirety.

BACKGROUND

The present disclosure relates to surgical instruments, including instruments for implantation of tissue, such as adipose tissue.

Autologous fat grafting has become increasing common and has numerous clinical applications. These application include facial contouring, breast reconstruction and/or augmentation, and other body-contouring procedures. In addition, autologous fat grafting has been found to have relatively low donor-site morbidity compared with other surgical options.

Unfortunately, autologous fat grafting continues to provide somewhat unpredictable outcomes. For example, the amount of adipose cell viability after implantation is variable, which can result in unacceptable outcomes and/or require multiple or revision procedures.

The reasons for the unpredictability in fat-graft outcomes are not completely understood. Some clinicians, however, have found a correlation between aspects of the surgical procedures used and ultimate graft viability. For example, J. H. Lee et al. have studied the correlations between aspiration pressure during graft collection, injection pressure, and sheer stress on graft viability. J. H. Lee et al., "The Effect of Pressure and Shear on Autologous Fat Grafting," *Plastic and Reconstructive Surgery*, May 2003: 1125-1136. Lee concluded that higher aspiration and injection pressures, up to a point, did not affect fat graft viability in vivo, but the degree of shear stress, which is a function of flow rate, did significantly affect fat graft viability. And fat grafts injected slowly with low shear stress outperformed grafts injected with high shear stress. Id.

Various instruments have been described to assist surgeons in controlling the amount of pressure or shear applied to fat grafts during collection and reinjection. For Example, US Patent Publication Number 2013/0158515 A1 to Austen, describes systems with sensors to measure and/or control pressure, shear, and injection velocity. Similarly, US Patent Publication Number 2012/0209248, describes systems for collection and injection of adipose tissue, which allow control of injection pressure below certain limits. These systems, however, may require expensive pre-assembled, costly, and complex devices, and require measurement of the fluid pressure directly developed within a syringe cavity. Accordingly, these systems may be inconvenient for wide use due to the expense and need for specialized equipment.

SUMMARY

The present disclosure provides devices and methods for injection of tissues, including adipose tissue grafts. The devices and methods can facilitate control injection variables to improve graft viability and quality.

According to certain embodiments, a surgical instrument is provided. The instrument can comprise a pressure sensor and a support body attached to the pressure sensor, wherein the support body includes an opening for receiving a proximal end portion of an injection instrument to secure the pressure sensor to the injection instrument such that the pressure sensor can provide a measurement indicative of a shear force exerted on a material contained within a cavity of the injection instrument during use.

The pressure sensor can be contained within a portion of the support body. The support body can comprise a substantially rigid outer wall. In some embodiments, the support body can further comprise a closure mechanism for surrounding the proximal end portion of the injection instrument to secure the support body to the pressure instrument.

The surgical instrument can also comprise a feedback mechanism configured to provide a signal to an operator indicative of the pressure exerted on a material contained within a cavity of the injection instrument during use. The feedback mechanism can include at least one mechanism selected from a vibration system, an optical system, and an auditory system. In certain embodiments, the feedback mechanism comprises a vibrating instrument operably attached to the support body and configured to provide a vibration to the surgical instrument when the pressure exerted on a material contained within a cavity of the injection instrument during use reaches a predetermined threshold. The feedback mechanism can also comprise a vibrating instrument operably attached to the support body and configured to provide a vibration that increases in intensity as the pressure exerted on a material contained within a cavity of the injection instrument increases beyond a predetermined threshold. In other embodiments, the feedback mechanism comprises an optical mechanism selected from a light, a flashing light, and a color indicator.

The surgical instrument can also comprise a calibration system configured to calibrate a signal provided by the pressure sensor based on a selected injection instrument. The calibration system can comprise an electrical controller. The electrical controller can be configured to control an output of the pressure sensor to control operation of a feedback mechanism. The injection instrument can comprise a syringe.

In other embodiments, a surgical instrument is provided. The instrument can comprise a pressure sensor; and a support body attached to the pressure sensor, wherein the support body includes a means for securing the pressure sensor to a proximal end portion of an injection instrument such that the pressure sensor can provide a measurement indicative of a pressure exerted on a material contained within a cavity of the injection instrument during use, and wherein the pressure sensor is not in fluid communication with the material contained within the cavity of the injection instrument.

The surgical instrument can further comprise a feedback mechanism configured to provide a signal to an operator indicative of the pressure exerted on a material contained within a cavity of the injection instrument during use. The feedback mechanism can include at least one mechanism selected from a vibration system, an optical system, and an auditory system. In some embodiments, the feedback mechanism comprises a vibrating instrument operably attached to the support body and configured to provide a vibration to the surgical instrument when the pressure exerted on a material contained within a cavity of the injection instrument during use reaches a predetermined threshold.

The surgical instrument can further comprise a calibration system configured to calibrate a signal provided by the pressure sensor based on a selected injection instrument. The calibration system can comprise an electrical controller. The electrical controller can be configured to control an output of the pressure sensor to control operation of a feedback mechanism. The injection instrument can comprise a syringe.

In some embodiments, a method of transplanting adipose tissue is provided. The method can comprise positioning an adipose tissue sample within a cavity of an injection device and securing a pressure sensor to a proximal end portion of an injection instrument such that the pressure sensor can provide a measurement indicative of a pressure exerted the adipose tissue within the injection instrument during use. The pressure sensor can be contained within a portion of a rigid support body.

The method can further comprise applying pressure to the injection instrument to inject adipose tissue into a selected tissue site and reducing the pressure in response to a signal received by a feedback mechanism configured to provide a signal to an operator indicative of the pressure exerted on an adipose tissue within the cavity of the injection instrument. The signal can comprise at least one of a vibration system, an optical signal, and an auditory signal. In some embodiments, the signal comprises a vibration when the pressure exerted on a material contained within a cavity of the injection instrument during use reaches a predetermined threshold. In some embodiments, the signal comprises a vibration when the pressure exerted on a material contained within a cavity of the injection instrument during use reaches a predetermined threshold, and wherein the vibration increases in intensity as the pressure on the adipose tissue increases.

The method can further comprise calibrating the pressure sensor to provide a signal related to the amount of pressure exerted on the adipose tissue and on the selected injection instrument. The calibration system can comprise an electrical controller, and the injection instrument can comprise a syringe.

BRIEF DESCRIPTION OF THE DRAWINGS

FIG. 3A illustrates a perspective view of a surgical instrument, according to various embodiments.

FIG. 3B illustrates a perspective view of a surgical instrument, according to various embodiments.

DETAILED DESCRIPTION

Figure 1:
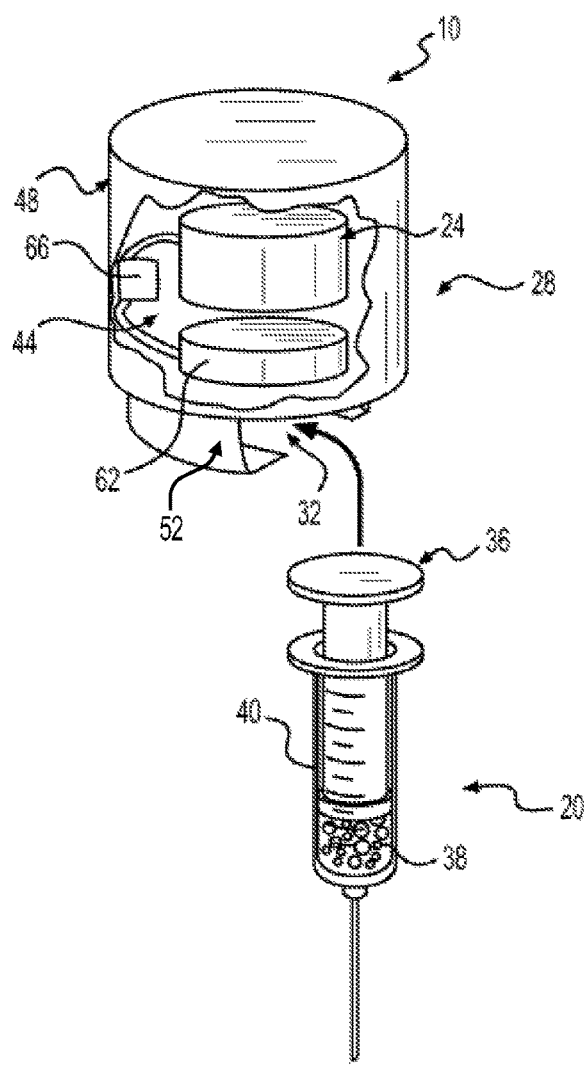
FIG. 1 illustrates a perspective cutaway view of a surgical instrument, according to various embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including," as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various human and animal tissues can be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. For example, fat grafting, including autologous fat grafting, can be useful for a variety of clinical applications including facial fillers, breast augmentation, buttock augmentation/sculpting, augmentation of other tissue sites, correction of lumpectomy defects, cranial-facial defect correction, correction of lipoplasty defects (divots).

Grafting of various tissues, however, can be unpredictable, resulting in variable outcomes and multiple procedures and/or revision surgeries. Although the precise reasons for graft variability are not always known, there is evidence that the viability of grafted cells, included grafted adipose tissues are affected by surgical techniques, including that amount of pressure and/or shear stress applied to the grafts when injected/implanted using injection devices such as syringes or similar systems that use needles or cannulas.

Control of grafting technique, however, can be complex. For example, it may be difficult for clinicians to determine the pressure and/or shear applied to grafts during a particular surgical procedure. This can be true for a variety of reasons. For example, the pressure and shear stress exerted on a sample can relate to a number of variables including the particular injection device used (e.g. syringe and needle/cannula size, injection rate, tissue tumescence, injection device material properties (e.g., friction properties), tissue viscosity, clogging of cannulas, and backpressure from a host site, or other mechanical properties. Accordingly, the present disclosure provides devices and methods to facilitate control of surgical procedures to improve graft outcomes.

In some embodiments, the devices and methods can be used for injection or implantation of adipose tissues, or any other live tissue that maintains some rate of viability after injection. As used herein, "adipose tissue" refers to adipose tissue obtained by any means, including, for example liposuction, standard tumescent liposuction. In addition, the adipose tissue may be substantially intact, or may be altered by, for example, washing with saline, antimicrobials, detergents, or other agents; modified by additional of therapeutic agents such an analgesics, antimicrobials, and anti-inflammatories; modified by removal of some cells or acellular components; and disrupted or altered by the collection, including, for example, during liposuction or tumescent liposuction.

Figure 2:
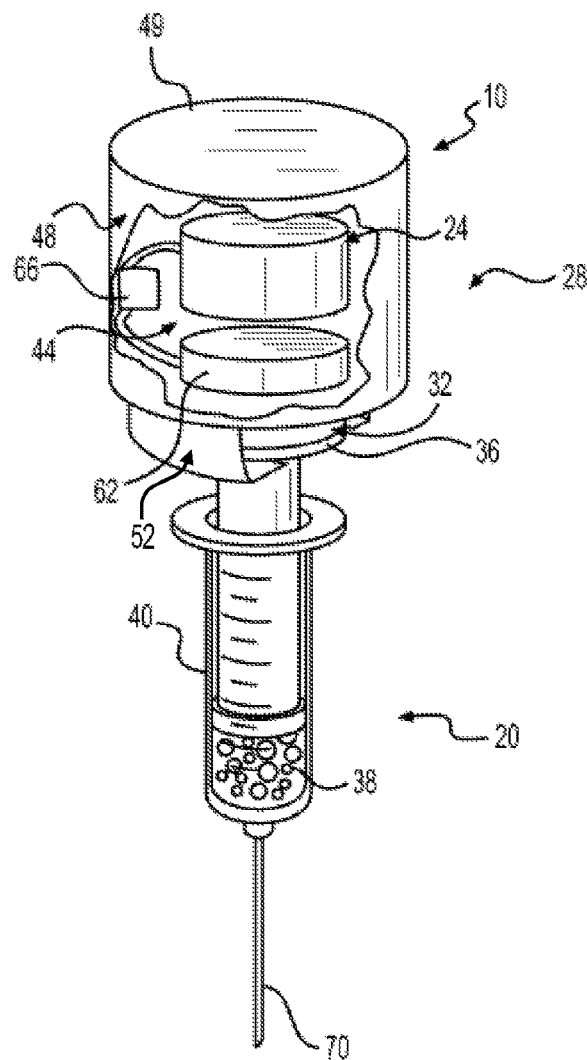
FIG. 2 illustrates a perspective cutaway view of a surgical instrument including an injection device, according to various embodiments.

According to certain embodiments, a surgical instrument is provided. FIG. 1 illustrates a perspective cutaway view of a surgical instrument 10 before attachment to an injection device, according to various embodiments, and FIG. 2 illustrates a perspective cutaway view of the surgical instrument 10 after attachment to an injection device 20, according to various embodiments.

The instrument 10 can comprise a pressure sensor 24; and a support body 28 attached to the pressure sensor 24. As discussed further below, the support body 28 can include an opening 32 for receiving a proximal end 36 portion of the injection instrument 20. As described further below, the opening 32 or suitable other attachment means can be configured to secure the pressure sensor 24 to the injection instrument 20 such that the pressure sensor 24 can provide a measurement indicative of a pressure exerted on a material 38 contained within a cavity 40 of the injection instrument 20 during use.

The pressure sensor 24 can be attached to the support body 28 in a number of ways. For example, the pressure sensor 24 can be contained within a portion 44 of the support body 28, or can be secured to the support body 28. Regardless of how the pressure sensor 24 is attached to the support body 28, the pressure sensor 24 and support body 28 are configured such that pressure applied to a proximal end 36 of the injection device to inject adipose tissue or other material 38 contained within the cavity 40 of the injection instrument 20 is transmitted to the pressure sensor, thereby allowing the pressure sensor to measure the force applied to the proximal end 36.

The support body can 28 be formed of a variety of materials and shapes. In some embodiments, the support body 28 is formed of a substantially rigid material, and the pressure sensor 24 is positioned relative to the body in such a way as to permit pressure applied to the proximal end 36 of the injection device 20 to be transmitted to the pressure sensor 24.

FIGS. 3A and 3B illustrate surgical instruments 10' and 10", according to certain embodiments. As shown, the instruments 10', 10" include support bodies 28', 28". In one embodiment, the pressure sensor 24 is attached to a top surface 26 of the support body 28' (FIG. 3A), so that when the support body is attached to the injection instrument 20, pressures is transmitted through the pressure sensor 24. In another embodiment, the support body 28" (FIG. 3B) has an opening to allow pressure to be applied to a pressure sensor 24 contained at least partially within a portion 44 of the support body 28", again allowing pressure to be transmitted through the pressure sensor 24. Although, not illustrated, each of surgical instruments 10', 10" can include other features described elsewhere herein, including a feedback mechanism, calibration systems, controllers, or other components.

The support body 28 can alternatively comprise an outer wall 48 (FIGS. 1 and 2), formed of a material that is compressible over at least a portion of its dimensions. For example, the outer wall 48 can comprise a viscoelastic housing that compresses as the support body 28 is compressed, thereby transmitting force applied to a top surface 49 through the pressure sensor 24 and into the injection instrument 20.

In some embodiments, the support body 28 can further comprise means 52 for securing the body 24 to the proximal end 36 of the injection instrument 20. In one embodiment, as shown in FIGS. 1, 2, and 3A-3B the means 52 allows the support body 28 to be secured to the proximal end portion 36 of the injection instrument 20 such that the pressure sensor 24 can provide a measurement indicative of a pressure exerted on the material 38 contained within the injection instrument 20 during use. In one embodiment, the pressure sensor 24 is not in fluid communication with the material 38 contained within the cavity of the injection instrument. As such, the surgical instrument 10 provides a modular pressure-sensing device that can be connected to a variety of different injection devices 20, and the surgical instrument 10 can be sold alone for later connection to a selected injection instrument 20, or as a kit along with an injection instrument 20 and/or other components.

As noted, the pressure sensor 24 can provide a measurement indicative of a pressure exerted on the material 38. It should be understood, however, that the pressure sensor may not directly measure the pressure exerted on the material 38, but may provide a pressure measurement related to the pressure on the material 38, but may simply be a measurement that can be correlated with the pressure or shear exerted on the material 38. As such, as described further below, the measurement can be used to produce a signal or output that can be correlated in such a way as to provide feedback to appropriately control injection pressure, rate, and/or shear.

Figure 4:
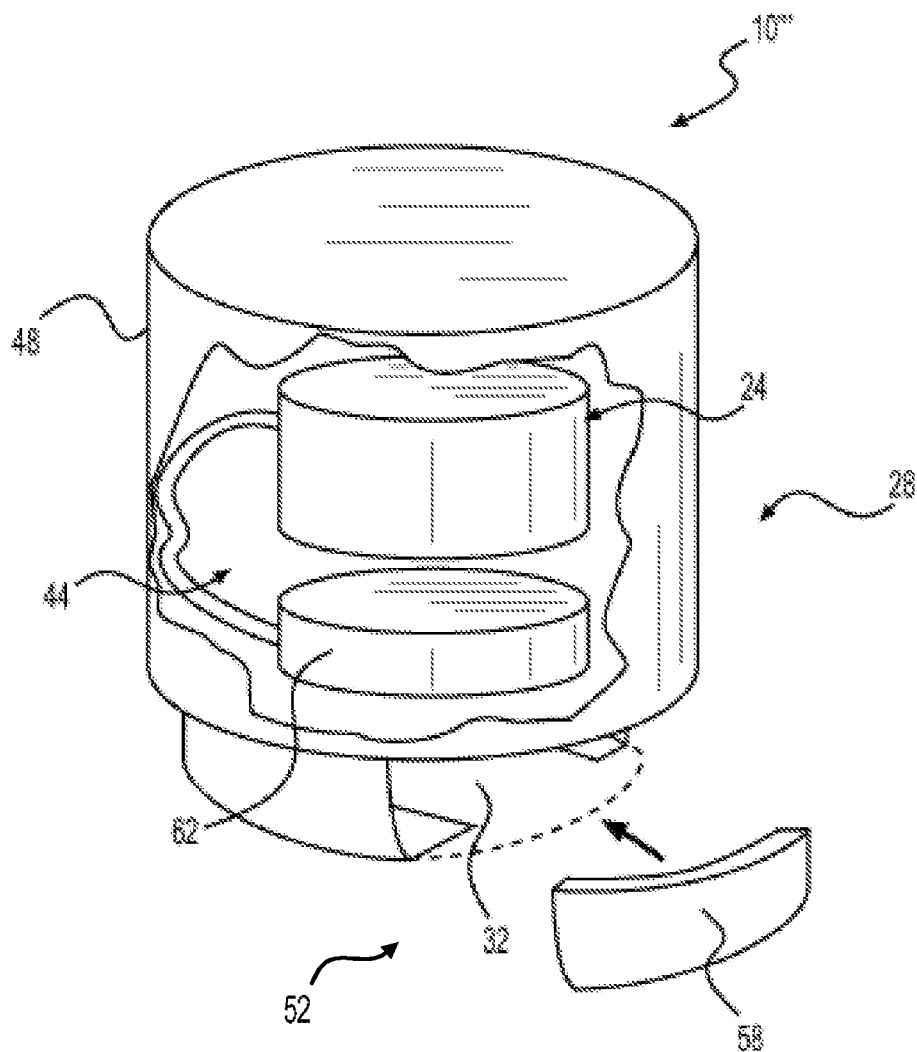
FIG. 4 illustrates a perspective view of a surgical instrument, according to various embodiments.

As noted above, the surgical instrument can include an opening 32 or suitable other means configured to secure the pressure sensor 24 to the injection instrument. In addition, the surgical instrument can include other components to be used along with or in an alternative to the opening 32. For example, the instrument 10''' can include any suitable a closure mechanism. A suitable closure mechanism can include a cap 58 (FIG. 4) to close the opening 32 to secure the supporting body 28 to the proximal end portion of the injection instrument 20. Alternatively, the means or closure mechanism can include a clip, bracket, clamp, threaded closure system, securing strap (e.g., to be wrapped around a portion of the instrument), an adhesive system (e.g., two-way tape), or other suitable mechanical attachment mechanism configured to secure the supporting body 28 to the injection instrument 20.

As noted above, the surgical instruments are configured to assist a surgeon in performing a surgical procedure, including implantation of adipose tissue grafts. To that end, the surgical instruments can further comprise a feedback mechanism 62 configured to provide a signal to an operator indicative of the pressure exerted on a material 38 contained within a cavity of the injection instrument during use. The feedback mechanism 62 can include at least one mechanism selected from a vibration system, an optical system, and an auditory system. In certain embodiments, the feedback mechanism 62 comprises a vibrating instrument operably attached to the support body 28 and configured to provide a vibration to the surgical instrument 10 when the pressure exerted on a material 38 contained within a cavity 40 of the injection instrument 20 during use reaches a predetermined threshold. The feedback mechanism 62 can also or alternatively comprise a vibrating instrument operably attached to the support body 28 and configured to provide a vibration that increases in intensity as the pressure exerted on a material 38 contained within a cavity 40 of the injection instrument 20 increases beyond a predetermined threshold. In other embodiments, the feedback mechanism 62 comprises an optical mechanism selected from a light, a flashing light, and a color indicator.

FIGS. 1 and 2 illustrate a suitable feedback mechanism 62. As shown, the feedback mechanism 62 may be contained within the support body 28 (e.g., beneath, next to, or on top of the pressure sensor 24). In addition the feedback mechanism 62, can be operably connected to the pressure sensor 24, e.g. through an electrical, mechanical, or electro-mechanical connection, such that the feedback mechanism 62 is activated at a desired pressure or shear exerted on the material 38 to provide appropriate feedback to a clinician.

The surgical instrument can also comprise a calibration system 66 configured to calibrate a signal provided by the pressure sensor 24 based on a selected injection instrument. Generally, the pressure sensor 24, feedback mechanism 62, and calibration system 66 will operate together to provide a signal to a clinician when a pressure exerted on material 38 contained within a cavity 40 of the injection instrument 20 reaches, approaches, or exceeds a predetermined threshold. The predetermined threshold may be determined based on a variety of factors described in more detail below, but generally including the structure of the particular injection instrument, tissue to be injected, and actual pressure exerted on the proximal end 36 of an injection instrument 20.

The calibration system 66 can include a variety of suitable controllers or mechanisms for controlling a signal generated by the pressure sensor 24 in response to an applied force so as to activate the feedback mechanism 62 at an appropriate pressure. For example, the calibration system 66 can comprise an electrical controller having electrical circuitry configured to activate the feedback mechanism 62 upon receipt of a signal indicating that a predetermined pressure has been applied to the pressure sensor or an certain shear stress has been applied to the material 38.

The devices described herein can be used with certain methods for transplanting adipose tissue. The method can comprise positioning an adipose tissue sample within a cavity of an injection device 10; and securing a pressure sensor to a proximal end 36 of an injection instrument 20 such that the pressure sensor 24 can provide a measurement indicative of a pressure exerted the adipose tissue within the injection instrument during use. The pressure sensor 24 can be contained within a portion of a support body 28.

The method can further comprise applying pressure to the injection instrument 20 to inject adipose tissue into a selected tissue site; and reducing the pressure in response to a signal received by a feedback mechanism 62 configured to provide a signal to an operator indicative of the pressure exerted on a adipose tissue within the cavity of the injection instrument. As noted above, the signal can comprise at least one of a vibration system, an optical signal, and an auditory signal. In some embodiments, the signal comprises a vibration when the pressure exerted on a material contained within a cavity of the injection instrument during use reaches a predetermined threshold. In some embodiments, the signal comprises a vibration when the pressure exerted on a material contained within a cavity of the injection instrument during use reaches a predetermined threshold, and wherein the vibration increases in intensity as the pressure on the adipose tissue increases.

The method can further comprise calibrating the pressure sensor 24 to provide a signal related to the amount of pressure exerted on the adipose tissue and on the selected injection instrument. A suitable calibration system 66 can comprise an electrical controller.

The specific injection instrument can include a variety of common or specially designed surgical instruments. For example, as shown in FIG. 2, the injection instrument 20 comprises a typical syringe, having a size and attached to a needle or cannula 70 with dimensions suitable for injection of adipose or other tissues.

In addition, although the present instruments and methods are described specifically for control of pressure when injecting adipose tissues, it will be appreciated that the devices and methods may be used with other suitable materials including other tissue types or products that may be subject to damage by excess pressure and/or shear. Further, the present device may be used to facilitate injection of other substances (e.g., medications, tissue fillers, dyes, contrast agents, or fluids), when control of the pressure may be important for appropriate delivery and/or to prevent damage to an implantation site.

What is claimed is:

1. A method of transplanting adipose tissue, comprising:
    positioning an adipose tissue sample within a cavity of an injection instrument; and
    securing a pressure sensor to a proximal end portion of the injection instrument such that the pressure sensor can provide a measurement indicative of a pressure exerted on the adipose tissue within the cavity of the injection instrument during use, the pressure sensor enclosed within a support body including an opening for receiving the proximal end portion of the injection instrument to secure the pressure sensor to the injection instrument, wherein the support body comprises a compressible outer wall such that application of pressure to the outer wall causes compression of the wall and transmission of force to the pressure sensor.

2. The method of claim 1, further comprising applying pressure to the injection instrument to inject adipose tissue into a selected tissue site; and
    reducing the pressure in response to a signal received by a feedback mechanism, wherein the feedback mechanism is configured to provide the signal to an operator indicative of the pressure exerted on the adipose tissue within the cavity of the injection instrument.

3. The method of claim 2, wherein the signal comprises at least one of a vibration, an optical signal, and an auditory signal.

4. The method of claim 3, wherein the signal comprises a vibration when the pressure exerted on the adipose tissue contained within the cavity of the injection instrument during use reaches a predetermined threshold.

5. The method of claim 3, wherein the signal comprises a vibration when the pressure exerted on the adipose tissue contained within the cavity of the injection instrument during use reaches a predetermined threshold, and wherein the vibration increases in intensity as the pressure on the adipose tissue increases.

6. The method of claim 1, further comprising calibrating the pressure sensor with a calibration system to provide a signal related to the amount of pressure exerted on the adipose tissue and on the selected injection instrument.

7. The method of claim 6, wherein the calibration system comprises one or more electronic controllers.

8. The method of claim 1, wherein the injection instrument comprises a syringe.

9. The method of claim 1, wherein the support body further comprises a closure mechanism to close the opening in the support body such that the support body and the closure mechanism completely surround the proximal end portion of the injection instrument.

10. A method of transplanting adipose tissue, comprising:
    positioning an adipose tissue sample within a cavity of an injection instrument;
    securing a pressure sensor to a proximal end portion of the injection instrument such that the pressure sensor can provide a measurement indicative of a pressure exerted on the adipose tissue within the cavity of the injection instrument during use, the pressure sensor enclosed within a support body including an opening for receiving the proximal end portion of the injection instrument to secure the pressure sensor to the injection instrument, wherein the support body comprises a compressible outer wall such that application of pressure to the outer wall causes compression of the wall and transmission of force to the pressure sensor; and periodically sensing an output from the pressure sensor using one or more electrical controllers.

11. The method of claim 10, wherein the support body is formed from a substantially rigid material.

12. The method of claim 10, wherein the support body comprises:
a closure mechanism to close the opening in the support body such that the support body and the closure mechanism completely surround the proximal end portion of the injection instrument.

13. The method of claim 10, further comprising applying pressure to the injection instrument to inject adipose tissue into a selected tissue site; and
reducing the pressure in response to a signal received by a feedback mechanism, wherein the feedback mechanism is configured to provide the signal to an operator indicative of the pressure exerted on the adipose tissue within the cavity of the injection instrument.

14. The method of claim 13, wherein the signal comprises at least one of a vibration system, an optical signal, and an auditory signal.

15. The method of claim 10, further comprising calibrating the pressure sensor with a calibration system to provide a signal related to the amount of pressure exerted on the adipose tissue and on the selected injection instrument.

16. The method of claim 15, wherein the calibration system comprises the one or more electronic controllers.

17. The method of claim 10, wherein the injection instrument comprises a syringe.

18. The method of claim 14, wherein the signal comprises a vibration when the pressure exerted on a material contained within a cavity of the injection instrument during use reaches a predetermined threshold.

19. The method of claim 14, wherein the signal comprises a vibration when the pressure exerted on a material contained within a cavity of the injection instrument during use reaches a predetermined threshold, and wherein the vibration increases in intensity as the pressure on the adipose tissue increases.

* * * * *